(12) United States Patent
Goldberg

(10) Patent No.: US 7,981,071 B2
(45) Date of Patent: Jul. 19, 2011

(54) APPARATUS AND METHOD FOR REDUCING PAIN DURING SKIN PUNCTURING PROCEDURES

(75) Inventor: Steven G. Goldberg, Boca Raton, FL (US)

(73) Assignee: Bing Innovations, LLC, Boca Raton, FL (US)

( * ) Notice: Subject to any disclaimer, the term of this patent is extended or adjusted under 35 U.S.C. 154(b) by 413 days.

(21) Appl. No.: 11/575,564

(22) PCT Filed: Sep. 19, 2005

(86) PCT No.: PCT/US2005/033769
§ 371 (c)(1),
(2), (4) Date: Mar. 19, 2007

(87) PCT Pub. No.: WO2006/034324
PCT Pub. Date: Mar. 30, 2006

(65) Prior Publication Data
US 2008/0255483 A1    Oct. 16, 2008

Related U.S. Application Data

(60) Provisional application No. 60/611,497, filed on Sep. 20, 2004, provisional application No. 60/707,754, filed on Aug. 12, 2005.

(51) Int. Cl.
*A61B 17/20* (2006.01)

(52) U.S. Cl. .......... 604/22; 433/117; 433/118; 433/119; 433/86; 128/200.16; 451/165; 451/910; 606/169; 606/171

(58) Field of Classification Search .................... 604/22; 433/117–118, 119, 86; 318/116, 118; 128/200.16; 606/169, 171, 177, 178
See application file for complete search history.

(56) References Cited

U.S. PATENT DOCUMENTS

| 2,258,857 | A | | 10/1941 | McCann |
| 3,620,209 | A | | 11/1971 | Kravitz |
| 4,091,805 | A | | 5/1978 | Clark |
| 5,636,988 | A | * | 6/1997 | Murayama .................... 433/118 |
| 5,639,238 | A | * | 6/1997 | Fishburne, Jr. ............... 433/215 |

(Continued)

FOREIGN PATENT DOCUMENTS
WO   03024513 A1   3/2003
WO   2004000196 A1   12/2003

OTHER PUBLICATIONS

International Search Report, published Feb. 11, 2006 for International Application No. PCT/US2005/033769, filed Sep. 19, 2005.

(Continued)

*Primary Examiner* — Theodore J Stigell
*Assistant Examiner* — Edelmira Bosques
(74) *Attorney, Agent, or Firm* — Martin Fleit; Paul D. Bianco; Fleit Gibbons Gutman Bongini & Bianco PL

(57) ABSTRACT

A handheld instrument for minimizing pain during administration by injection of a liquid, such as, an anesthetic that has a main body, a vibration unit mounted in the main body when initiated to cause the main body to vibrate, and a detachable tip cantilever mounted on the main body to vibrate with it, the tip having a free end characterized by a bifurcation to form two spaced projections defining a space between them, whereby the spaced projections can be placed in proximity to, adjacent to and bracketing a preselected injection site on a human or animal and the tissue at said preselected injection site and vibrated while an injection is given.

15 Claims, 7 Drawing Sheets

U.S. PATENT DOCUMENTS

| | | | |
|---|---|---|---|
| 5,704,902 A * | 1/1998 | Vandenbelt et al. | 601/72 |
| 5,928,170 A * | 7/1999 | Garrigan | 601/47 |
| 6,030,210 A * | 2/2000 | Bianchetti | 433/29 |
| 6,355,007 B1 | 3/2002 | Zuckerbrod | |
| 6,602,229 B2 | 8/2003 | Coss | |
| 2002/0082564 A1 * | 6/2002 | Pham | 604/192 |
| 2003/0040714 A1 | 2/2003 | Coss | |
| 2004/0077977 A1 | 4/2004 | Ella et al. | |

OTHER PUBLICATIONS

International Preliminary Report on Patentability, published on Mar. 20, 2007 for International Application No. PCT/US2005/033769, filed Sep. 19, 2005.

Written Opinion of the International Search Authority published on Mar. 20, 2007 for International Application No. PCT/US2005/033769, filed Sep. 19, 2005.

International Search Report published on Nov. 2, 2006, for PCT/US2005/33769, filed Sep. 19, 2005.

International Preliminary Report on Patentability published Mar. 20, 2007, for PCT/US2005/33769, filed Sep. 19, 2005.

Written Opinion published on Mar. 20, 2007, for PCT/US2005/33769, filed Sep. 19, 2005.

Supplementary European Search Report dated May 18, 2010 for Application No. EP05803150, pp. 1-5.

* cited by examiner

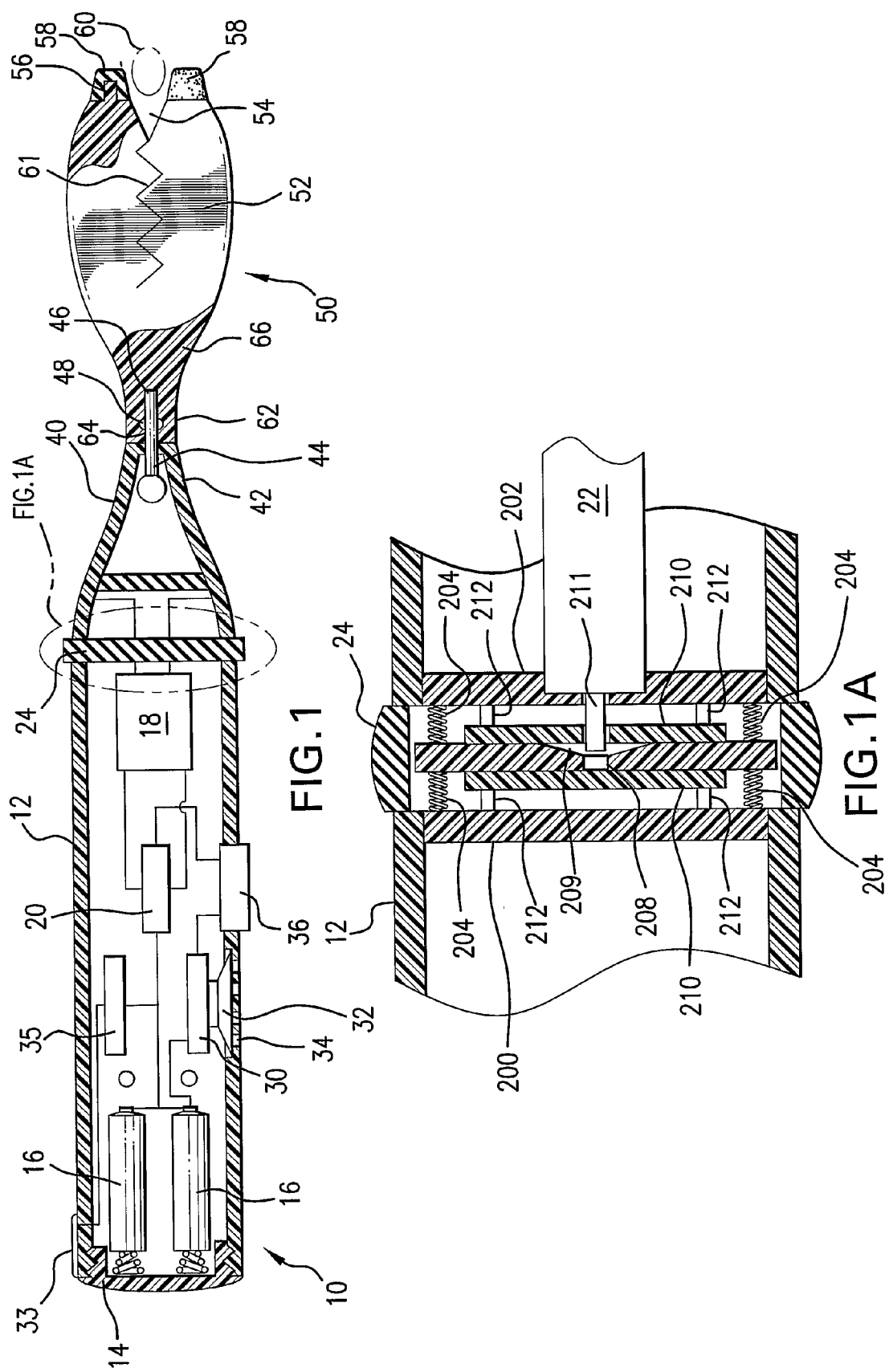

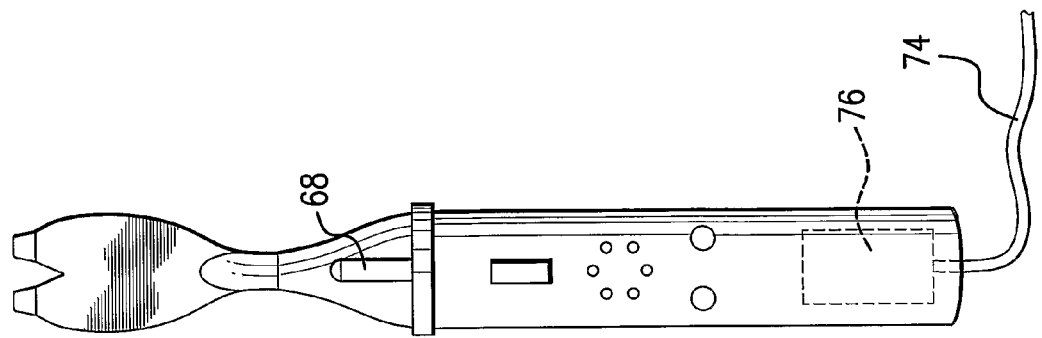
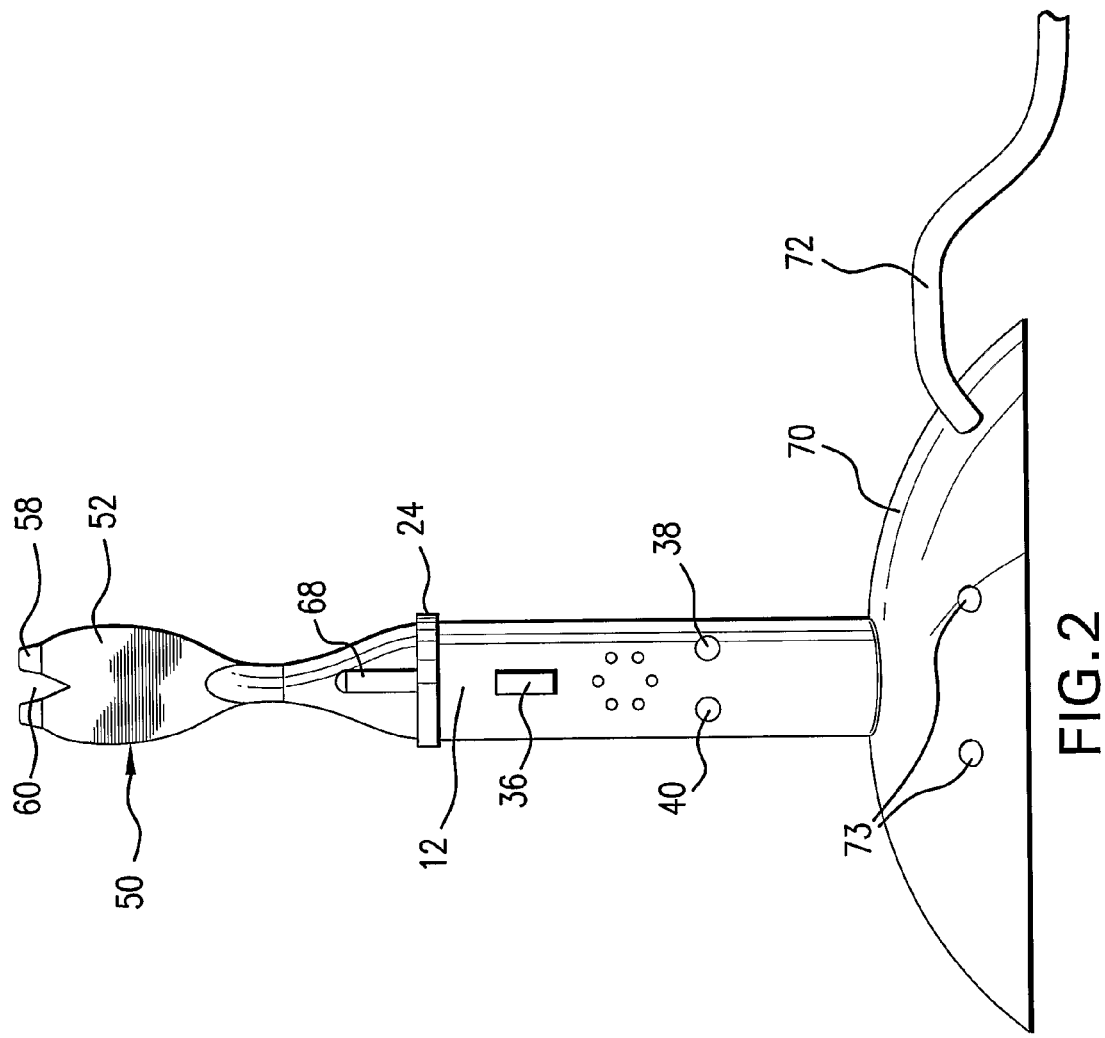

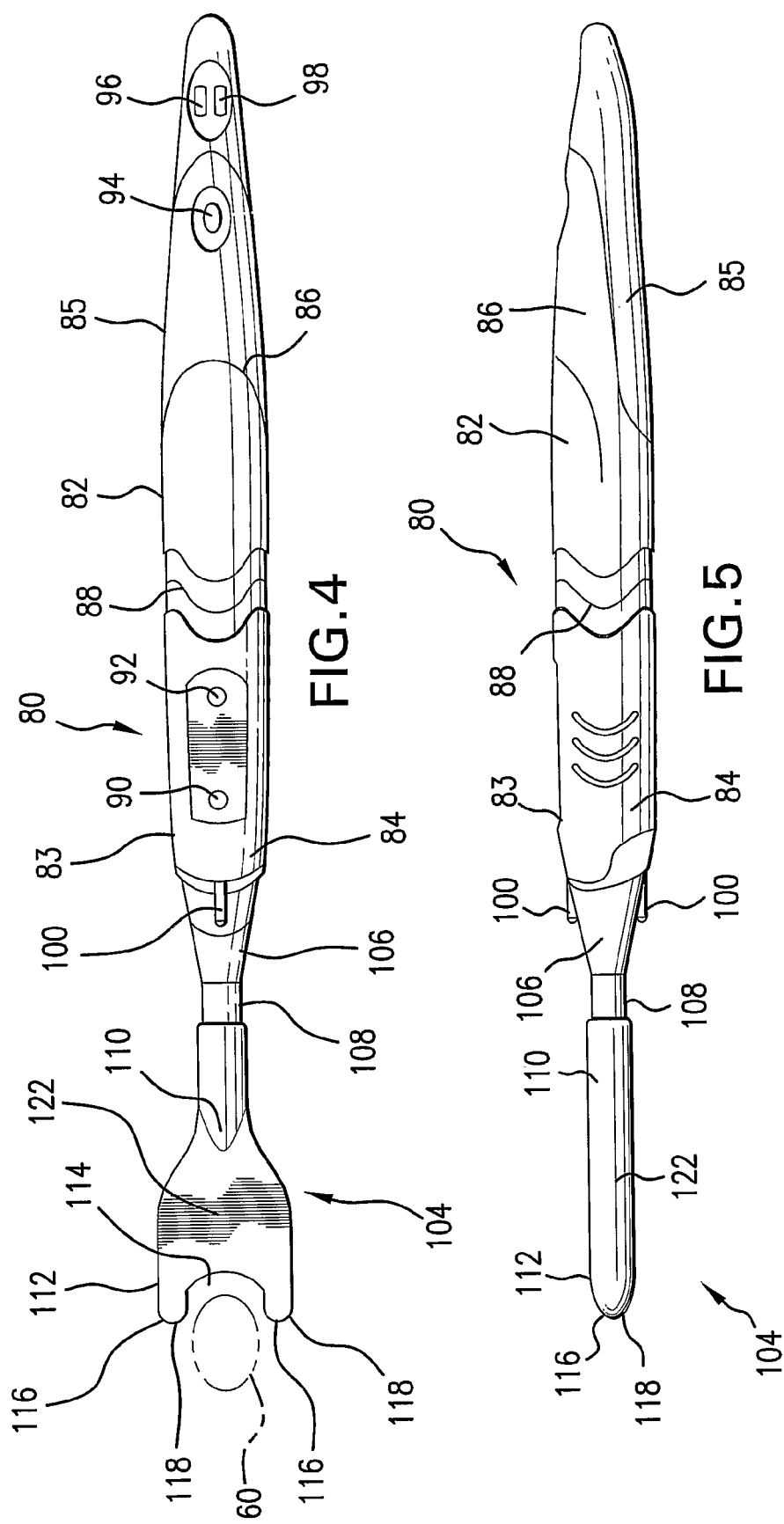

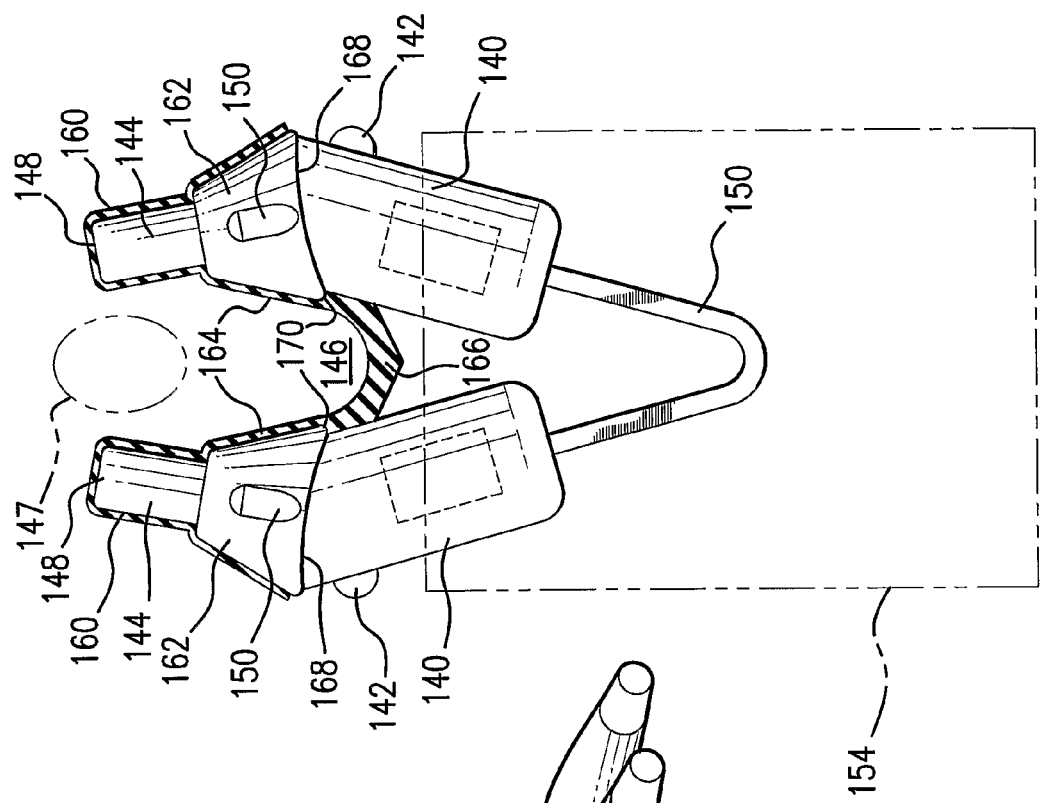
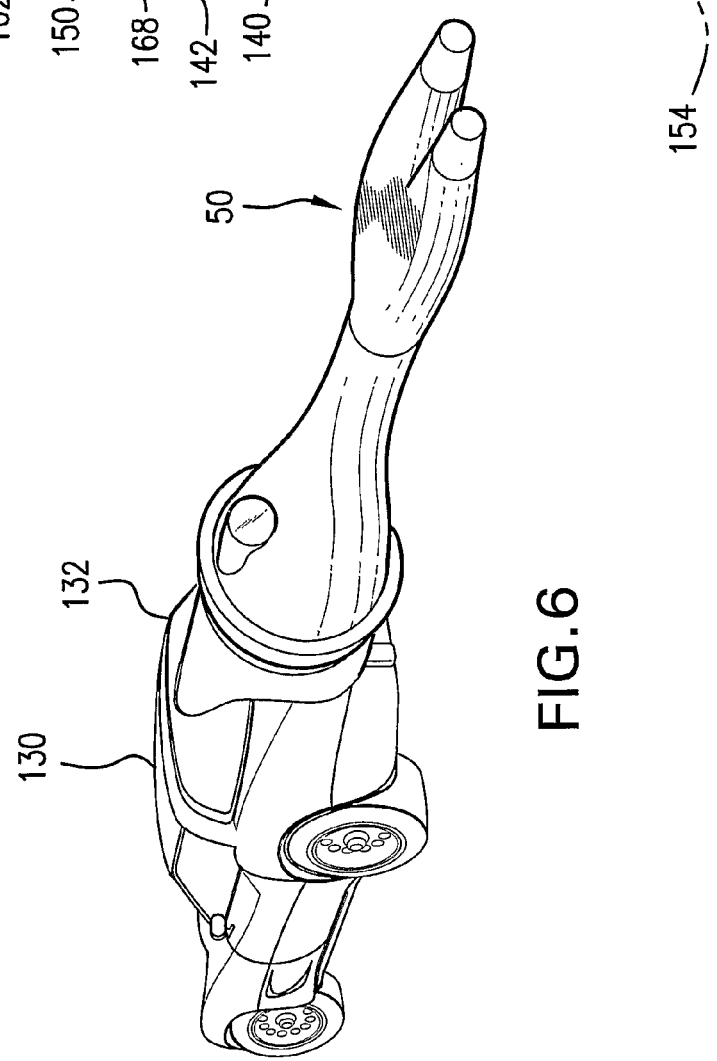
FIG.6
FIG.7

APPARATUS AND METHOD FOR REDUCING PAIN DURING SKIN PUNCTURING PROCEDURES

FIELD OF INVENTION

The invention relates to a method and apparatus for use in medical and dental procedures, and particularly to a method and apparatus in the form of a retractor vibrator for reducing or minimizing pain during skin puncturing procedures, such as, administration by injection, into the gums, skin or other tissue of a patient, of a liquid, such as, and in particular, an anesthetic.

BACKGROUND OF THE INVENTION

In the prior art, the normal procedure for reducing the pain when injecting a liquid, such as, an anesthetic, serum, vitamins, vaccine, or other medical or dental efficacious liquids is either to (a) place a very cold material against the skin or flesh of the patient at the injection site, (b) to apply a topical treatment to the skin or flesh at the injection site, which temporarily numbs the skin or flesh (c) rapidly manually massaging the skin or tissue at the injection site while performing the injection. Although these procedures have some effect, they are either cumbersome, require some time to complete or are of limited effect and do not reduce the pain to a satisfactory level.

SUMMARY OF THE INVENTION

In view of the disadvantages of the prior art, it is a general object of the present invention to provide a method and apparatus in the form of a retractor vibrator, the use of which will overcome those disadvantages when injecting an anesthetic, serum, vitamins, vaccine, or other medical or dental efficacious liquids. In particular, it is an object of the present invention to provide an apparatus and method which can be easily and inexpensively utilized during a medical, veterinary or dental procedure to almost completely or substantially eliminate the pain attendant an injection as it punctures the skin or flesh of the patient.

In keeping with the objects of the present invention, the present invention comprises a method and a hand-held apparatus, in its preferred form of a retractor vibrator, for vibrating at least two skin or tissue areas immediately adjacent and bracketing an injection site simultaneously with injection by needle of a liquid, such as, an anesthesia, serum, vitamins, vaccine, or other medical or dental efficacious liquids, into the skin or tissue at the injection site. Such a typical injection procedure may involve an injection of Novocain into a patient's gum or other tissue during a dental procedure.

Accordingly it is an object of the invention to provide an instrument for minimizing pain during administration by injection of a liquid, such as, an anesthetic comprising a main body, a vibration unit mounted in the main body when initiated to cause the main body to vibrate, and a detachable tip cantilever mounted on the main body to vibrate with it, said tip having a free end characterized by a bifurcation to form two spaced projections defining a space between them, whereby the spaced projections can be placed in proximity to, adjacent to and bracketing a preselected injection site on a human or animal and the tissue at said preselected injection site vibrated while an injection is given.

As further objects of the invention an instrument as above can be arranged wherein the detachable tip includes a paddle to act as a retractor, wherein a 360° control switch is provided on the main body for on/off control of the vibration unit, wherein a music player is included in the main body for playing music through a speaker, wherein the main body includes rechargeable batteries as a power source to drive the vibration unit, wherein lights are provided on the main body directed toward the space defined between the spaced projections, wherein the paddle is split to define two portions each being capable of vibrating independently, wherein caps are received on the two spaced projections, and/or wherein the surface of the paddle is reflective.

Another object of the invention includes an instrument comprising two elongated housings coupled at one end by a resilient V-shaped bar, the forward ends of the housings spaced from one another and terminating in free ends which define a space therebetween, a sterile removable cap on the free ends, a vibration unit mounted in each housing when actuated to vibrate the main body including the free ends, whereby the spaced capped free ends can be placed in proximity to, adjacent to and bracketing a preselected injection site on a human or animal and the tissue at said preselected injection site vibrated while an injection is given Another object of the invention includes an instrument comprising a main body, a pair of arms having free ends pivoted to the main body and resiliently biased apart, a stop for limiting the separation of the free ends of the arms so that a space is defined between them, a sterile removable cap received on each free end, whereby the spaced capped free ends can be placed in proximity to, adjacent to and bracketing a preselected injection site on a human or animal and the tissue at said preselected injection site vibrated while an injection is given.

Still a further object of the invention is to provide an instrument comprising a main body, a pair of arms having free ends mounted on the main body, the free ends of the arms projecting away from the main body so that a space is defined between them, the free ends of said arms defining sterile contact areas, whereby the sterile contact areas can be placed in contact with skin or tissue in proximity to, adjacent to and bracketing a preselected injection site on a human or animal and the contacted skin or tissue vibrated while an injection is given. The instrument described can be arranged wherein the pair of arms are fixed in a structure that is attached to the main body, and alternatively the structure is detachably coupled to the main body. Also the instrument can be arranged wherein the sterile contact areas are defined by removable coverings or are defined by coatings of FDA approved soft plastic. Also, another object of the invention includes a method comprising the steps of vibrating tissue of a human or animal in proximity to, adjacent to and bracketing a preselected injection site while simultaneously injecting by a needle or like instrument a liquid at the preselected injection site. The bracketing can be at spaced locations relative to the injection site. The bracketing can also be on opposite sides of the injection site.

BRIEF DESCRIPTION OF THE DRAWINGS

The above-mentioned features and objects of the present invention will be discussed in terms of the attached figures wherein like reference numerals denote like elements and in which:

FIG. 1 is a drawing partly in section of an embodiment of the apparatus of the present invention;

FIG. 1A shows a cross section through the handle of the apparatus shown in FIG. 1, showing the details of a 360° switch employed;

FIG. 2 shows the apparatus of the present invention positioned in a charger;

FIG. 3 is a elevational view illustrating a modification of the apparatus of FIG. 1;

FIG. 4 is a top plan view of a second, preferred, embodiment of the apparatus of the invention;

FIG. 5 is a side view of the second embodiment shown in FIG. 4;

FIG. 6 is a perspective view showing how the apparatus is inserted in a toy or model;

FIG. 7 shows a third embodiment of the apparatus of the invention suitable for a medical application with the apparatus shown inserted in a toy or model shown in dotted line;

DETAILED DESCRIPTION OF PREFERRED EMBODIMENTS OF THE INVENTION

Figure 8:
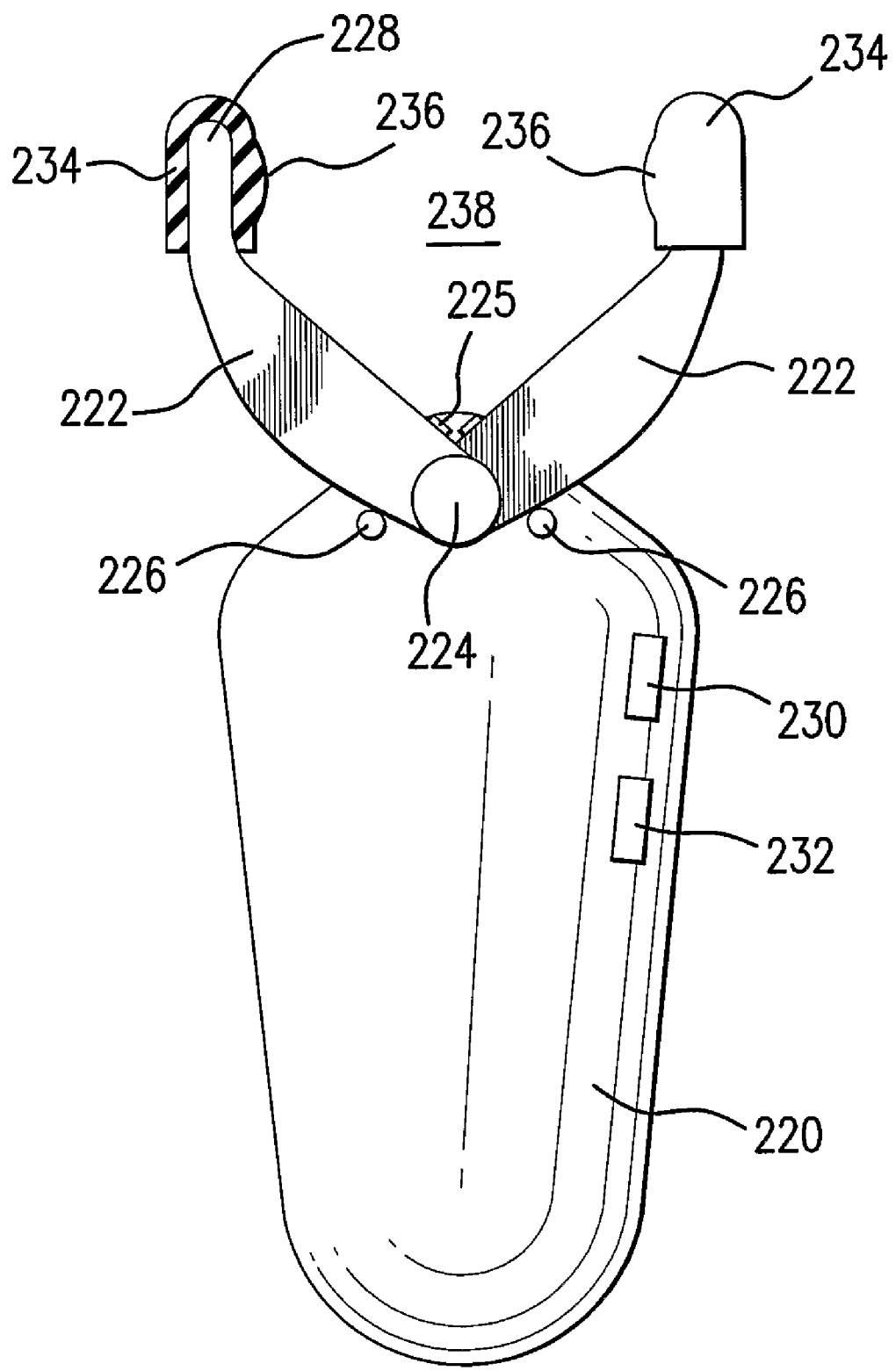
FIG. 8 shows a fourth embodiment of the apparatus of the invention suitable for a medical application.

Referring to FIG. 1, a retractor vibrator is shown generally designated as 10 for performing the functions of the present invention, as will be explained hereinafter. In particular, retractor vibrator 10 is a handheld apparatus comprising a main body or handle 12 in the shape of a tube having an end closure 14 that is threaded to screw onto the open end of tube 12 complementarily fitted. Handle 12 is composed of hard plastic. Rechargeable batteries 16, two being used, power a known vibrator unit 18, shown schematically, that is fixed in the handle 12 and when actuated, causes the handle 12 and everything mounted on it to vibrate, in the nature of a vibrating electric toothbrush. A suitable circuit 20, shown schematically, connects with the vibrator 18 via an on/off switch 22 incorporated in part in a resilient collar 24 extending 360° to enable actuation of the switch in any hand position on the handle 12. Alternatively, a simple on/off switch can be used. The vibrator 18 may be any known vibrator existing in the prior art which is capable of providing vibratory energy at a suitable vibratory frequency and intensity, such as the vibration unit of an electrically operated toothbrush as is currently on the market. Typical devices include piezoelectric devices connected to sources of ultrasonic frequency signals and rotating motors with offset weights.

Also contained within the handle 12, shown schematically, is a music recorder/player 30 that is loaded with a recording that plays through a speaker 32 situated in the handle 12 behind perforations 34. A switch 36 is provided suitably connected to turn the recorder 30 on/off to initiate the recording and shut it off. The recorder/player can also be integrated into the switch 24 so that when the unit is turned on, the music plays, and when the unit is turned off the music stops playing. The handle 12 is also provided with two lights 38 (green to show adequately charged) and 40 (amber to show in need of charging) that are connected in the circuit 20 to monitor the condition of the batteries 16. Contacts 33 for charging the batteries 16 are mounted on the exterior of handle 12 at the rear, and connected via a known and suitable charging unit 35 to the batteries 16.

The front end of the handle 12 has a tapered transition section 40 that tapers down to a smaller tube 42 in which a projection 44 is fixedly mounted that extends outwardly to provide a mounting post 46 having slightly raised bosses 48 on which to position an elongated disposable sterilized tip 50. The disposable tip 50 is a retractor vibrating component, composed of opaque hard plastic, comprises, at its rear end, a tubular section 62 that is provided with a central opening 64 extending in the longitudinal axial direction of the tip 50. The tip 50 is placed on the handle by fitting the projection 44 into the tip opening 64 and pressing so that the tip 50 is securely held by friction by the slight raised bosses 48, but can be pulled off readily when desired.

The front end of tip 50 is comprised of a transition section 66 extending from the tubular section 62 and transitions from round to a generally flat retractor paddle 52 formed with a V recess 54 and terminating with two stubs 56 extending forwardly and spaced apart, the concept being that the two stubs 56 are able to lie adjacent to and bracket a proposed injection site 60, shown in dotted lines, in close proximity therewith and on opposite sides of the injection site 60. Rubber caps 58 are opaque and cover the stubs 56, and are intended as the vibrating contact points with the tissue or skin being contacted. The retractor paddle is split at zigzag line 61 to enable the two split portions of the paddle to vibrate independently in a plane normal to the plane of the paddle 52. The preferred vibration imparted to the paddle is in the plane normal to the paddle 52. The split may be omitted so the paddle is integrally one component.

A pair of lights 68, preferably LEDs are mounted 180° apart on the front end of handle 12 directed over the top surface (plane) and bottom surface (plane) of the flat paddle 52, pointed or aimed at the V-space 54 between the rubber caps 58, i.e. to illuminate the injection site 60 (SEE FIGS. 2 and 3). The lights 68 turn on and off with the actuation of the switch 22 which controls the vibrator unit 18. When the vibration unit 18 is powered, the handle 12 and the tip 50 vibrate, and therefore, the rubber caps 58 vibrate. Since the caps 58 are intended to be in contact with the skin or tissue in close proximity to and adjacent to and bracketing an injection site 60, the vibrations of these areas, bracketing the injection site 60, act to minimize and reduce pain which might result from a needle being inserted into the skin or tissue at the injection site.

The apparatus of FIG. 1 is shown in FIG. 2 positioned or mounted in a charging unit 70, of conventional design and consisting of a mounting base or platform to receive the handle 12 with the contacts suitably electrically engaged for charging. A line 72 connects the charging unit 70 to an AC voltage outlet, e.g. a 110 volt outlet, for charging. A pair of lights 73 (one being green and one being red denoting the standard activity and condition of the charger) are mounted on the charger. Vibrator unit 18 is powered by the rechargeable batteries 16 serviceable to be changed when necessary, by unscrewing bottom end of the handle at closure 14. As explained, the handle 12 has a projection 44 sticking out of the top end of the unit which vibrates and allows a disposable retractor vibrator tip 50 to be detachably snapped on over the projection (bosses 48). Although a snap fit is described, the detachable connection between the disposable tip 50 and the end of the handle 12 could be a press fit or a bayonet fit, or any other suitable detachable connection. The retractor vibrator unit 10 contains two headlights 68, one on each side of the retractor tip 50, aimed toward the rubber nodes or caps 58. The retractor vibrator 10 has a squeezable on/off switch 24 near the top end. This switch 24 wraps circumferentially 360 degrees around the unit. It is pressed and released for on, and pressed and released for off. The retractor vibrator 10 also contains a vibrating unit 18 and a musical box 30 with speaker 32 which plays a melody and has its own on/off switch 36.

Disposable retractor vibrator tip 50 is made of hard, resilient plastic, with or without a rubber or other coating. In the most preferred arrangement, the paddle surface is reflective, and may be hard plastic that is white and reflective or covered by a reflective film. It has 2 caps or nodes 58 on the end, preferably hard rubber but could be any comparable material that won't dampen vibrations and is not hard plastic, which vibrate when unit 18 is turned on. The paddle 50 serves as a retractor which maintains the injection site 60 free and accessible. For example, if the retractor vibrator is inserted into a patient's mouth in order to administer an injection near the gum line, the paddle 50 will hold the cheek retracted. This entire retractor paddle 50 will vibrate and includes the 2 rubber nodes 58. The paddle 50 will be from about one-sixteenth of an inch in thickness to about one-quarter inch in thickness and used to retract the lip or cheek while administering a Novocain type injection. The 2 nodes 58 will make contact with the soft or hard tissue in the mouth at the same time. This will cause a vibratory stimulus to the nerves adjacent to and bracketing the injection site 60, exciting the nerves in the immediate area resulting in a relatively painless injection. Charging unit 70 is where vibrating unit will be stored when not in use. The invention is applicable to humans as well as animals.

FIG. 1A shows in detail the 360° switch. The handle 12 has a wall 200 just to the rear of the resilient collar 24, and a wall 202 just forward of the collar 24. Springs 204 are attached at one end to the walls 200 and 202, as shown in FIG. 1A, and attached at their other end to a disc 206 that sits in the plane of collar 24 with small clearance. Thus the disc 206 will essentially float in the space beneath the collar 24. The center of disc 206 is cutout at 208, and the portion surrounding the cutout is tapered to provide a circular inclined surface 209. Two smaller diameter plates 210 are fixed or suspended from the walls 200 and 202 by struts 212 to abut the disc 206 in a manner that allows disc 206 to move radially relative to the two guide plates 210. Switch 22 is positioned in the conical section 40 and is held at its rear in the wall 202. The actuator rod 211 for switch 22 extends freely through wall 202 and plate 210 with it free end 213 lying in the plane of the disc 206. When collar 24 is pushed radially inwardly, the disc 206 will be contacted at its periphery and pushed or shifted radially, regardless of the angular location of the contact between the collar 24 and the disc 206. Thus, the incline portion 209 will strike the actuator rod 211 causing it to move axially into the switch 22 to actuate switch 22 to turn on, if off and to turn off, if on.

The embodiment shown in FIG. 1 is primarily used for dentistry, but may be used in a medical application. The dental retractor vibrator is preferably about 7 inches long, the handle being about 5 inches long and the disposable tip 50 being about 2 inches long, and about ¾ inches to 1 inch in diameter. The width of the nodes 58 is from about ⅟₁₆ to about ¼ inches with about ³⁄₁₆ inches preferred, and the spacing between the nodes 58 is from about ⅛ inches to about 1 inch with ⅜ inches being preferred. The paddle width is from about ½ inch to about 1.5 inches wide.

FIG. 3 shows a hardwired model provided with a line 74 to connect to a AC voltage source and powering via circuit 76 the vibration unit.

As noted, a charger is provided, which may be any conventional charger. Preferably, the charger is of the inductive type in which the end of the handle 12 is inserted into a cylindrical opening of the charger. The cylindrical opening is surrounded by a coil and recharging energy is transferred from the coil surrounding the opening 14 to the transfer charge device in the handle 12 which provides the recharging energy to the batteries 16.

Referring now to FIGS. 4 and 5, a most preferred of the preferred embodiments for the dental application is shown. The dental unit 80 consists of a handle 82 composed of hard plastic that is provided with soft plastic covering at 84 and 86 for better gripping. A seam 88 is provided in handle 82 to enable the front end 83 to be separated from the rear end 85 to enable battery replacement. The details of the inside of the handle are omitted for the sake of clarity as the inside contains the same components as shown in FIG. 1, a vibration source, batteries, a music recorder/player, a speaker and a suitable interconnecting and control circuit to perform the functions described. Switch buttons 90 and 92 are provided to turn the vibration unit on and off, respectively. A switch 94 is provided to turn the music player on/off. Two small metal panels 96 and 98 are provided for battery recharging indicated as + and − poles. A pair of ultra bright LED bulbs 100 are provided on opposite sides of the handle directed over the disposable tip 104 to light the area of the injection. An acoustic hole is provided (not shown) for music out from the mini-speaker positioned inside the handle 82 in alignment with the hole. The front end of handle 82 is provided with a hard plastic transition section 106 having a projection extending forwardly similar to what is described in conjunction with FIG. 1 (not shown) for detachably mounting the disposable tip 104 in a suitable cantilevered manner, such as described for mounting tip 50 in conjunction with FIG. 1. The disposable tip 104 is comprised of a hard plastic bone 108 formed to coact with hard plastic section 106 for mounting in a detachable manner, as described. The bone 108 is covered by a soft FDA approved plastic or rubber coating 110. The free end 112 of tip 104 is bifurcated by a U-shaped recess 114 to define two forwardly extending projections 116 that are rounded 118 at their free ends. The projections 116 are so formed that they will lie in proximity to, adjacent to and bracket an injection site 120 that is positioned at least partially in the recess 114.

The dental unit of FIGS. 4 and 5 is preferably about 215 mm long with the disposable tip being about 70 mm long and the handle being about 16.5 mm in diameter. The disposable tip 104 is shaped with a flat paddle portion 122 to serve as a retractor that at its rear transitions into a cylindrical section to mate and mount on section 106. The operation of the dental retractor vibrator is apparent from the description of FIG. 1 and will not be further elaborated.

FIG. 6 illustrates a dental unit combined with a toy in a manner useful for taking care of children for the purpose of distracting them while performing an injection. The toy is shown as an automobile 130, the rear of which has an opening 132 in which to insert the retractor vibrator 10 or 80 of either FIG. 1 or FIG. 4 in a manner that the projecting portion of the instrument enables the dentist access to the control button for on/off and to be able to use the disposable tip 50 or 104 effectively. When the procedure is finished, the retractor vibrator can be removed form the toy and the toy given to the child. Any suitable toy can be used for this purpose, such as a doll, a fire truck and the like, as long as it is modified to receive the retractor vibrator in a detachable manner.

FIG. 7 illustrates a medical application of the invention, that is, to some part of the body other than the mouth. The medical unit consists of a pair of hard plastic housings 140, each containing a vibration source, batteries, a music recorder/player, a speaker and a suitable interconnecting and control circuit to perform the functions described. Each has its own switch 142 which needs to be depressed to initiate vibration and held depressed to continue vibrating. When switch 142 is released, the vibration is turned off. The forward end of each housing 140 is angled inwardly at an acute angle, e.g. 30°, toward the space 146 (wherein injection site 147 is at least partially located) that separates the two housings 140, with the terminal end of each housing 140 provided with a projecting cantilevered post 144 having a free end 148. The rear end of the housings 140 are resiliently coupled together by a V-shaped bar of hard plastic 152 to provide a resilient coupling whereby the two housings 140 can be pushed toward each other and when released, return to the condition shown in the figure. Lights are optional for the two housings 140, and if present are at the position indicated by the reference numeral 150, and are directed to the space 146. The dot-dash line indicates a toy into which the unit can be inserted for the purposes described in conjunction with FIG. 6.

A sterile resilient disposable covering 154 is placed over the posts 144 and consists of two caps 160 that cover the posts 144 and the conical forward ends 162 of the housings 140. The two caps, in the area of space 146 are interconnected by a web 164 that has a thickened portion 166 to engage the conical forward ends 162 and bear on the main portion of housings 140. The juncture 168 between conical sections 162 and the main body of the housings 140 defines a shoulder 179 that provides an undercut to help hold the disposable covering on the unit and to shield the unit from contact with the injection site. Alternatively, simple sterile resilient caps 160 can be placed on the posts 144 only to just cover them. The covering can be soft FDA approved plastic or rubber. The principal use for the unit described above is medical to inject into a skin area. The capped posts 144 are placed in proximity to, adjacent to and bracketing an injection site 147, e.g. on a person's arm, and the buttons 142 are depressed to make each housing 140 vibrate, the housings 140 are pushed against the skin and flesh and slightly toward each other compressing the skin and flesh around the injection site, and while vibrating, the injection is effected. Referring to FIG. 8, a further embodiment of the medical apparatus is shown. The main body 220 of the medical unit is configured to fit in the palm of a human hand, like a computer mouse. Wishbone-shaped arms 222 are pivotally attached to the main body 220 by means of a pivot pin 224. The arms 222 mounted on the pivot pin 224 under the influence of a resilient force, e.g. a leaf spring 225 coiled around the pivot pin 224 and bearing on the arms 222 to urge them apart to the position shown in the figure. Suitable stops 226 can be provided to hold the position of the arms 222 as shown in the figure. The arms 222 cantilever upwardly, as shown in the figure and terminate in free ends 228. All components thus far described are composed of hard plastic, except for the spring force provided to resiliently urge the arms apart. The details of the inside of the body 220 are omitted for the sake of clarity as the inside contains the same components as shown in FIG. 1, a vibration source, batteries, a music recorder/player, a speaker and a suitable interconnecting and control circuit to perform the functions described. Switch buttons 230 and 232 are provided to turn the vibration unit on and off, respectively.

A pair of sterile caps 234 having enlarged facing bosses 236 is received detachably over the free ends 228 of the arms 222. Caps 234 are composed of a soft FDA approved sterile plastic or hard rubber.

In use, the patient's tissue which is to be vibrated is placed between the ends 228 of the wishbone arms 228. The operator squeezes the arms 228 together bringing the vibration tips or caps 236 and bosses 236 in contact with the tissue and close to one another and in proximity with, adjacent to and bracketing the site of the intended injection. The vibration unit is activated, and the vibration energy is delivered to the caps or tips 234 and transferred to the tissue. The tissue is at the location of an injection site which is at least partially within the space 238 between the arms 222. While the tissue is being vibrated in this manner, the injection is given.

It should be apparent to one skilled in the art, from the above description that the present invention can be utilized in a variety of procedures requiring a skin or flesh puncture. Such other procedures include such things as inoculations, shots to give patients medication, etc. Such skin punctures procedures can be performed on any portion of the body such as the arm, legs, buttocks, torso, etc.

The method of the invention consists in vibrating tissue of a human or animal in proximity to, adjacent to and bracketing a preselected injection site on the human or animal body while simultaneously injecting by a needle or like instrument a liquid at the preselected injection site. The bracketing is on spaced locations relative to the injection site, and preferably on opposite sides of injection site.

Figure 9A:
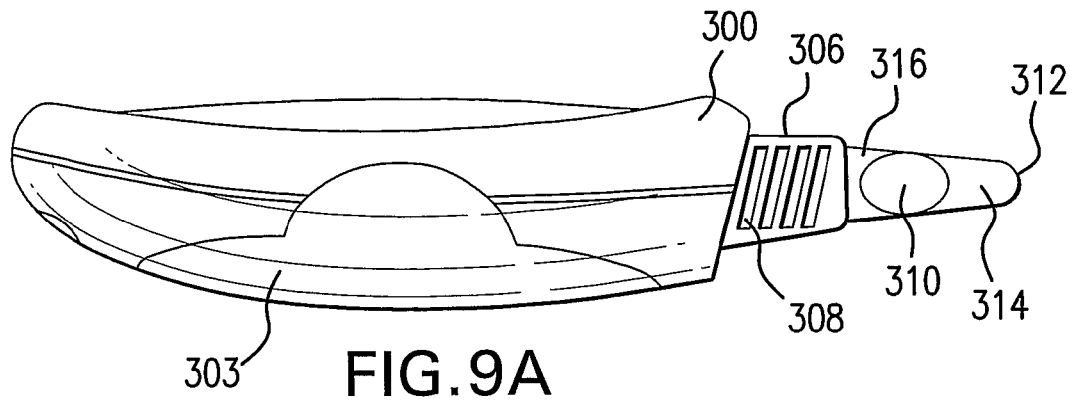
FIGS. 9A, B and C show respectively, a fifth embodiment of the invention in a side view, a top view and a bottom view.
Figure 9B:
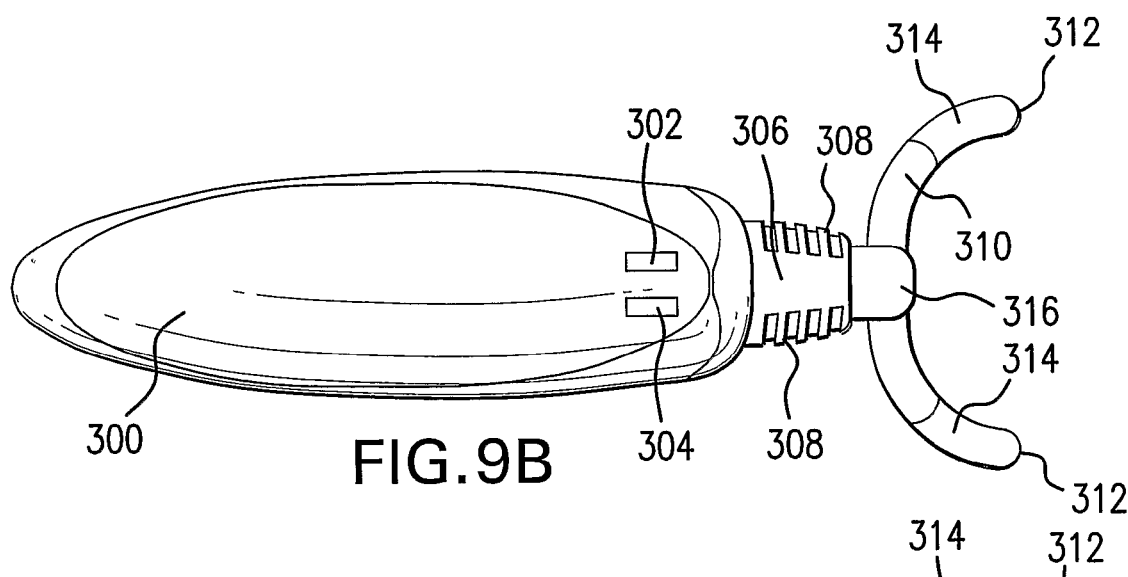
Figure 9C:
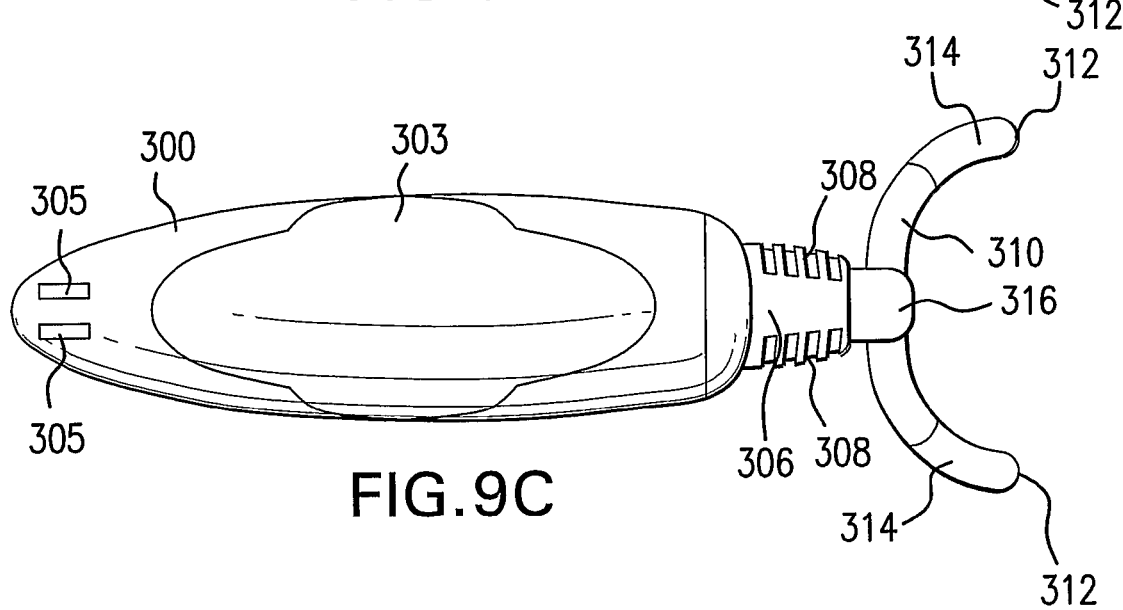

Referring now to FIGS. 9A, B and C, a fifth embodiment is shown as comprised of a main body 300 made of a hard plastic in the general shape of a computer mouse that houses the relevant components described above with respect to FIG. 1. The details of the inside of the body 300 are omitted for the sake of clarity, as the inside contains some or all of the same components as shown in FIG. 1, a vibration source, batteries, a music recorder/player, a speaker and a suitable interconnecting and control circuit to perform the functions described. Switch buttons 302 and 304 are provided to turn the vibration unit on and off, respectively. The hard plastic of the main body is covered, as shown in the drawing, with soft plastic covering 303 for enhancing the gripping of the main body by hand. Contacts 305 for battery charging are shown in FIG. 9C. Optionally, lights can be mounted at the front end of the main body in the manner of the embodiment of FIG. 1, but are omitted from the drawing for the sake of clarity. The forward end of the main body 300 terminates in an open ended tubular conical projection or cone 306 that on its surface defines opposed series of parallel ridges 308. A hard plastic core 310 in a shallow U-shape, akin to a cow's horns, is covered on both tips 312 with an FDA approved soft plastic covering 314. At the mid-point of the core 310 there is projecting a solid cylindrical stub 316 that is received in the open end of the projection 306 and held therein in any suitably clipped detachable manner. The core 310 is sterile and disposable, or alternatively could be provided with sterile and disposable removable coverings for the tips 312. The conical projection 306 coacts with the stub 316 to clip the stub 316 detachably in the projection 306, for example, by press fit, by detent, by internal bayonet fit, or any other suitable means that will be readily apparent to one of ordinary skill in the art, and requires no further elaboration. In one form, pressing the ridges 308 together can provide enough movement to release a clipped stub 316. Activation of the vibrating unit in the main body 300 causes the entire instrument to vibrate. The legs or "horns" of core 310 will be vibrated and they are of sufficiently flexibility to be brought toward each other slightly, so that skin or tissue between them can be placed under slight compression or pressure while an injection is made. The injection site is in the space between the tips 312. The skin or tissue in proximity, adjacent to and bracketing the injection site is slightly compressed and vibrated by the tips 312 during the injection. The core 310 and the parts attached to it are disposable, so that after use, it can be discarded and a new sterile core 310 can be inserted into the cone 306. Or as mentioned previously, disposable sterile coverings can be placed over the tips 312 for each use, and the core 310 retained intact.

Figure 10A:
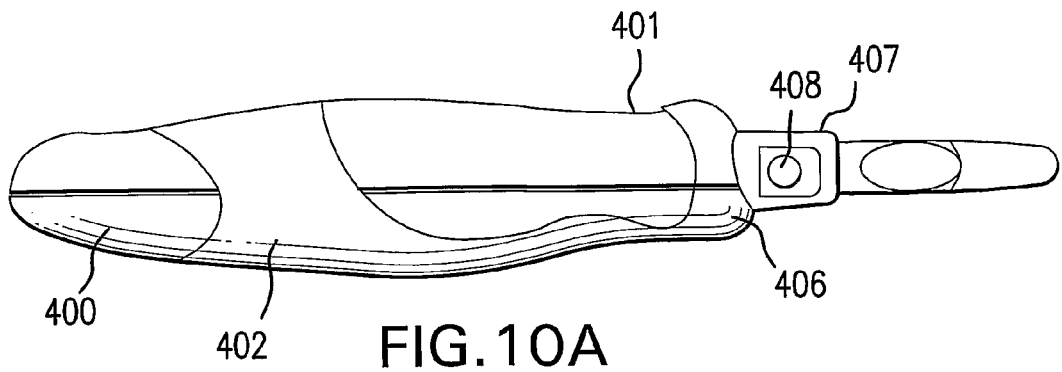
FIGS. 10A, B and C show respectively, a sixth embodiment of the invention in a side view, a top view and a bottom view.
Figure 10B:
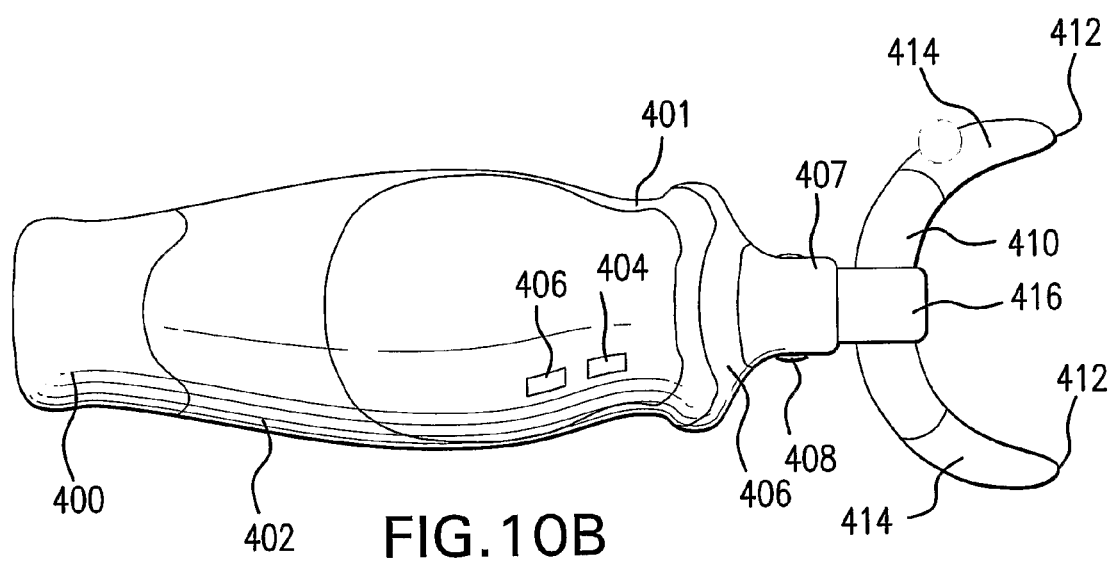
Figure 10C:
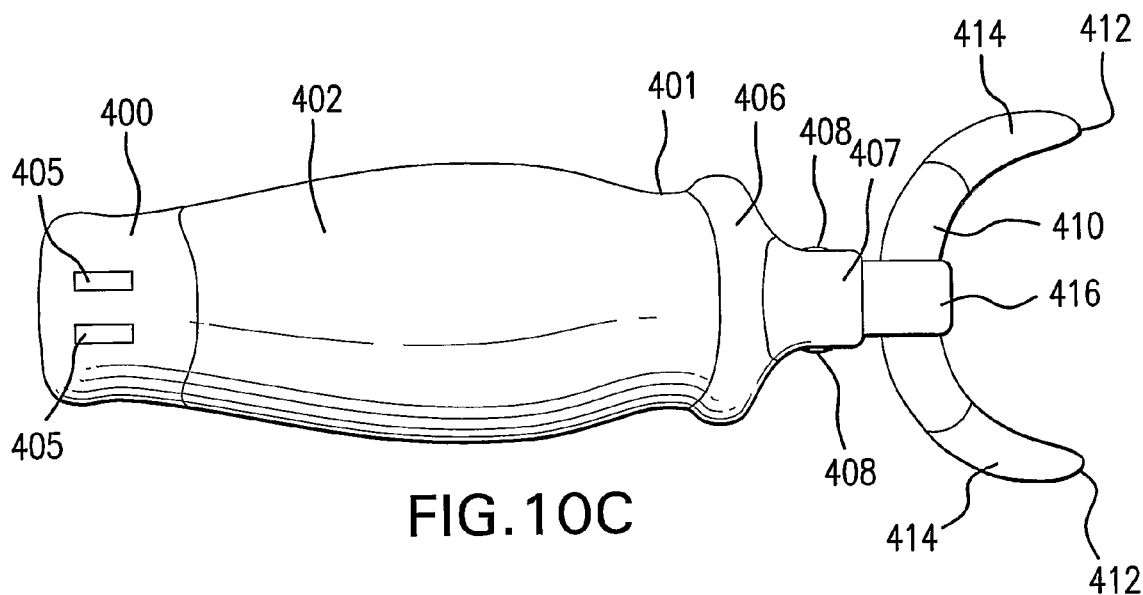

Referring now to FIGS. 10A, B and C, a sixth embodiment is shown as comprised of a main body 400 made of a hard plastic in a suitable ergonometric shape to fit more comfortably in a human hand. The main body is necked-down at 401 for this purpose. The main body 400 houses the relevant components described above with respect to FIGS. 1 and 9. The details of the inside of the body 400 are omitted for the sake of clarity, as the inside contains some or all of the same components as shown in FIG. 1, a vibration source, batteries, a music recorder/player, a speaker and a suitable interconnecting and control circuit to perform the functions described. Switch buttons 404 and 406 are provided to turn the vibration unit on and off, respectively. The hard plastic of the main body is covered, as shown in the drawing, with soft plastic covering 402 for enhancing the gripping of the main body by hand. Contacts 405 for battery charging are shown in FIG. 10C. Optionally, lights can be mounted at the front end of the main body in the manner described with reference to the embodiment of FIG. 1, but are omitted from the drawing for the sake of clarity. The forward end of the main body 400 terminates in an open ended projection 406 that includes tubular cylindrical projection or tube 407. Buttons 408 are mounted in opposite sides of tube 407 that are spring biases to normally intrude into the space in the tube 407 but will retract when the buttons are pressed inwardly. A hard plastic core 410 in a shallow U-shape, akin to a cow's horns, is covered on both tips 412 with an FDA approved soft plastic covering 414. At the midpoint of the core 410 there is projecting a solid cylindrical stub 416 that is received in the open end of the tube 407; core 401 has a groove adjacent its free end to coact with the buttons 408 in a known manner to detachably clip the core 410 in the tube 404. The core 410 is sterile and disposable, or alternatively could be provided with sterile and disposable removable coverings for the tips 412. The tube 407 coacts with the stub 416 to clip the stub 416 detachably in the tube 407 in the manner described. However, this can be done for example, by press fit, by detent, by internal bayonet fit, or any other suitable means all of which are known and readily apparent to one of ordinary skill in the art, and requires no further elaboration. Activation of the vibrating unit in the main body 400 causes the entire instrument to vibrate. The legs or "horns" of core 410 will be vibrated and they are of sufficiently flexibility to be brought toward each other, so that skin or tissue between them can be placed under slightly compression or pressure while an injection is made. The injection site is in the space between the tips 412. The skin or tissue in proximity, adjacent to and bracketing the injection site is slightly compressed and vibrated by the tips 412 during the injection. The core 410 and the parts attached to it are disposable, so that after use, it can be discarded and a new sterile core 410 can be inserted into the tube 407. Or as mentioned previously, disposable sterile coverings can be placed over the tips 412 for each use, and the core 310 retained intact.

While the present invention has been shown and described herein in what are conceived to be the most practical and preferred embodiments, it is recognized that departures, modifications, adaptations and variations may be made therefrom without departing from the intended scope of the invention as set forth in the appended claims.

What is claimed is:

1. An instrument for minimizing pain during administration by injection of a liquid, such as, an anesthetic comprising
   (a) an elongated main tubular body having a rear end and a forward end; (b) a vibration unit mounted in the main body to transmit vibrations;
   (c) a detachable elongated tip composed of hard plastic and having a rear portion and a forward portion;
   (i)
   the rear portion of said tip configured and dimensioned to match and be mountable on the forward end of the main body;
   (ii) said tip, via said rear portion, being cantilever coaxially detachably mounted on the forward end of the main body so that the tip extends axially forwardly and terminates in a free end;
   (iii) the forward portion of said tip adjacent its free end transitioning to a retractor portion;
   (d) two spaced, forwardly extending, short projections of hard plastic spaced between about ⅛ inch to about 1 inch apart and of smaller cross section than the cross section of the free terminal forward end of said elongated tip for receiving vibrations transmitted from the vibration unit in the main body, each said projection having a rear end fixed to the free terminal forward end of said tip and extending forwardly and terminating in a free rounded end, said projections lying in close proximity while defining a free space therebetween;
   (e) a soft plastic or rubber coating covering the free forward end of each said projection;
   (f) whereby the free forward ends of the two forwardly extending spaced projections of the detachable tip covered by soft plastic or rubber coatings can directly contact tissue at a proposed injection site on a human or animal and vibrate the tissue while an injection is given juxtaposed to the spaced projections.

2. An instrument according to claim 1 wherein a control switch is provided on the main body for on/off control of the vibration unit.

3. An instrument according to claim 1 wherein a music player is included in the main body for playing music through a speaker.

4. An instrument according to claim 1 wherein the main body includes rechargeable batteries as a power source to drive the vibration unit.

5. An instrument according to claim 1, further comprising a light to illuminate a space between the two projections.

6. An instrument according to claim 1 wherein the two projections vibrate independently.

7. An instrument according to claim 1 wherein the tip includes a retractor that is reflective.

8. An instrument according to claim 1 further including a toy having a recess into which the instrument is detachably received so that the detachable tip and the forward end of the main body of the instrument that holds the tip project out of the toy and can be operated.

9. An instrument according to claim 1 wherein the main body includes a projection onto which said tip is cantilever coaxially detachably mounted.

10. An instrument for minimizing pain during administration of a liquid by injection, the instrument comprising:
    a main body having a rear end and a forward end;
    a vibration unit mounted in the main body to transmit vibrations;
    a detachable tip having a rear section and a front end, the rear section being detachably mounted on the forward end of the main body to extend forward axially and to receive the vibrations transmitted from the vibration unit, the front end of the detachable tip comprising two forwardly extending spaced projections that define a preselected injection site in a space in close proximity to the two forwardly extending spaced projections, the two forwardly extending spaced projections of the detachable tip being spaced between about ⅛ inches to about 1 inch apart,
    wherein the detachable tip is configured to retract any overlapping tissue or skin to expose the preselected injection site and the tissue at the preselected injection site while the two forwardly extending spaced protections are in contact with tissue in close proximity to and bracketing the preselected injection site on a human or animal, and the two forwardly extending spaced projections of the detachable tip are configured to simultaneously vibrate to provide vibratory stimulus to facilitate pain reduction while an injection is being administered to the preselected injection site.

11. An instrument according to claim 10 wherein a control switch is provided on the main body for on/off control of the vibration unit.

12. An instrument according to claim 10 wherein the main body includes rechargeable batteries as a power source to drive the vibration unit.

13. An instrument according to claim 10, further comprising a light to illuminate the preselected injection site.

14. An instrument according to claim 10 wherein the two forwardly spaced projections vibrate independently.

15. An instrument according to claim 10 further including a toy having a recess into which the instrument is detachably received so that the detachable tip and the forward end of the main body of the instrument that holds the tip project out of the toy and can be operated.

\* \* \* \* \*